US010163200B2

(12) United States Patent
Heilmann

(10) Patent No.: US 10,163,200 B2
(45) Date of Patent: Dec. 25, 2018

(54) DETECTION OF ITEMS IN AN OBJECT

(71) Applicant: Smiths Heimann GmbH, Wiesbaden (DE)

(72) Inventor: Geert Heilmann, Wiesbaden (DE)

(73) Assignee: SMITHS HEIMANN GMBH, Wiesbaden (DE)

( * ) Notice: Subject to any disclaimer, the term of this patent is extended or adjusted under 35 U.S.C. 154(b) by 0 days.

(21) Appl. No.: 15/128,873

(22) PCT Filed: Mar. 24, 2015

(86) PCT No.: PCT/EP2015/056259
§ 371 (c)(1),
(2) Date: Sep. 23, 2016

(87) PCT Pub. No.: WO2015/144706
PCT Pub. Date: Oct. 1, 2015

(65) Prior Publication Data
US 2017/0103513 A1     Apr. 13, 2017

(30) Foreign Application Priority Data
Mar. 24, 2014 (DE) .......................... 10 2014 205 447

(51) Int. Cl.
*G06T 7/00* (2017.01)
*G01N 23/04* (2018.01)
(Continued)

(52) U.S. Cl.
CPC .......... *G06T 7/0004* (2013.01); *G01N 23/04* (2013.01); *G01V 5/0041* (2013.01);
(Continued)

(58) Field of Classification Search
CPC .......... G06T 7/0004; G06T 7/12; G06T 7/68; G06T 2207/10116; G06T 2207/30112;
(Continued)

(56) References Cited

U.S. PATENT DOCUMENTS 6,088,423 A * 7/2000 Krug .................... G01V 5/0041
378/4
6,711,293 B1 3/2004 Lowe
(Continued)

FOREIGN PATENT DOCUMENTS

| DE | 202007019256 U1 | 1/2012 |
|---|---|---|
| EP | 1522878 A1 | 4/2005 |

(Continued)

OTHER PUBLICATIONS

International Preliminary Report on Patentability (English Translation) dated Sep. 27, 2016 for PCT/EP2015/056259.
(Continued)

*Primary Examiner* — Brenda C Bernardi
(74) *Attorney, Agent, or Firm* — Kevin E. West; Advent, LLP

(57) ABSTRACT

This disclosure relates to a system and method for detecting an item having at least one symmetry property inside an inspection object based on at least one transmission image. The method includes the steps: (a) detection of edges of individual items contained in the transmission image in order to produce an edge image; and (b) detection of the item by determining a symmetry line that can be associated with an item with at least one symmetry property contained in the transmission image based on pairs of edge picture elements of the edge image that are positioned symmetrically to each other relative to the symmetry line; and in step (b), in determining the symmetry line in the edge image, the only edge picture elements that are taken into account are those for which the symmetry line lies in an item contained in the transmission image, to which item the edge belongs.

17 Claims, 8 Drawing Sheets

(51) Int. Cl.

| | | |
|---|---|---|
| *G01V 5/00* | (2006.01) | |
| *G06K 9/52* | (2006.01) | |
| *G06T 7/12* | (2017.01) | |
| *G06T 7/68* | (2017.01) | |
| *G06K 9/46* | (2006.01) | |

(52) U.S. Cl.
CPC ............. *G06K 9/4609* (2013.01); *G06K 9/52* (2013.01); *G06T 7/12* (2017.01); *G06T 7/68* (2017.01); *G01N 2223/206* (2013.01); *G01N 2223/401* (2013.01); *G06K 2209/09* (2013.01); *G06T 2207/10116* (2013.01); *G06T 2207/30112* (2013.01)

(58) Field of Classification Search
CPC ................. G01V 5/0041; G01N 23/04; G01N 2223/401; G01N 2223/206; G06K 9/52
See application file for complete search history.

(56) References Cited

U.S. PATENT DOCUMENTS

| | | | | |
|---|---|---|---|---|
| 7,986,841 B2* | 7/2011 | Wang | ................ | G06T 7/13 382/166 |
| 8,116,428 B2* | 2/2012 | Gudmundson | ........ | G01N 23/04 378/53 |
| 2003/0190011 A1* | 10/2003 | Beneke | ................ | G01V 5/0016 378/57 |
| 2005/0123217 A1* | 6/2005 | Schmiegel | ........... | G01V 5/0016 382/291 |
| 2006/0182218 A1* | 8/2006 | An | ................ | G01N 23/04 378/57 |
| 2011/0007870 A1* | 1/2011 | Roux | ................ | G01N 23/04 378/57 |
| 2011/0222779 A1 | 9/2011 | Karanam et al. | | |
| 2011/0235917 A1* | 9/2011 | Wu | ................ | G06T 7/13 382/190 |
| 2012/0275646 A1 | 11/2012 | Drouin et al. | | |
| 2012/0300078 A1* | 11/2012 | Ogata | ................ | G08G 1/166 348/148 |
| 2015/0199560 A1* | 7/2015 | Gokturk | ........... | G06K 9/00281 382/195 |

FOREIGN PATENT DOCUMENTS

| | | |
|---|---|---|
| EP | 2375375 A1 | 10/2011 |
| EP | 2696196 A1 | 2/2014 |
| WO | 2008149357 A2 | 12/2008 |

OTHER PUBLICATIONS

International Search Report dated Jun. 16, 2015 for PCT/EP2015/056259.
Li, Wai Ho et al., "Real Time Detection and Segmentation of Reflectionally Symmetric Objects in Digital Images", Proceedings of the 2006 IEEE/RSJ, International Conference on Intelligent Robots and Systems, Oct. 9-15, 2006, Beijing, China, pp. 4867-4873.
Lowe, David G., "Distinctive Image Features from Scale-Invariant Keypoints", International Journal ofo Computer Vision, Jan. 5, 2004, pp. 1-28.
International Preliminary Report on Patentability dated Sep. 27, 2016 for PCT/EP2015/056259.

* cited by examiner

DETECTION OF ITEMS IN AN OBJECT

TECHNICAL FIELD

The present disclosure generally relates to the nondestructive inspection of objects by means of ionizing radiation. In particular, the present disclosure relates to a method for detecting items having a symmetry property in an image of the object produced by means of ionizing radiation, particularly in an image of a piece of luggage, for example an X-ray image produced by an X-ray inspection system.

BACKGROUND

Some X-ray inspection systems have a plurality of fixed irradiation planes for nondestructive inspection of objects (inspection objects). An inspection of this kind can be carried out, for example, in the context of security screening of luggage at airports. During the inspection, an inspection object is conveyed through the plurality of irradiation planes that are each output by a respective stationary radiation source. The intensities of X-rays that are not absorbed by the inspection object and its contents are measured by detector arrays associated with the radiation sources. The intensity values measured are evaluated and used, among other things, for producing X-ray images of the inspection object, based on which a screening of the contents of the inspection object can be carried out.

Particularly with regard to an automated screening, containers such as bottles that are carried in luggage are problematic. Bottles can contain dangerous liquids. This is why liquids can only be brought aboard aircraft in small quantities, if at all. In the prior art, when performing security screening of hand luggage at airports, security personnel must first recognize such containers in X-ray images and then have to remove them from the luggage for a visual inspection. This additional inspection effort causes delays in passenger handling. This is similarly problematic with checked-in luggage. There, too, a piece of luggage must, for example, be removed from automatic handling and brought to a manual inspection station where it may be necessary to open the piece of luggage for a visual inspection and if need, additional inspections may be necessary. This also causes delays.

Some methods for identifying items (blobs) contained in an inspection object and to be found in an X-ray image of the object. For more precise identification, the detected blobs are inspected, among other things, for symmetry. Similarly to this, a bottle may be placed in a special box before X-raying so that the bottle is oriented at a known angle relative to the surface on which it is standing so that for an evaluation of the X-ray image of the bottle with regard to a possible threat potential of its contents, all geometric information with regard to the position of the bottle are known.

SUMMARY

The present disclosure relates to a method for automatically detecting or discovering containers in an X-ray image produced by means of an X-ray inspection of an object such as a piece of luggage. Further, the present disclosure relates to a device for carrying out the method.

Features and details that are described in connection with the method according to the present disclosure naturally also apply in connection with the device or X-ray inspection system and vice versa; consequently, each refers to the other with regard to the disclosure of individual aspects.

A core concept of the present disclosure lies in identifying regions in an X-ray image of an object based on the recognition of symmetry properties as belonging to an item contained in the object. In other words, the intent is to use an X-ray image of the object to discover items with symmetry properties that are contained in the object. If a container is detected, then based on the knowledge about the present container, the subsequent method makes it possible to draw an inference about the contents of the container, e.g. a liquid, and thus about a possible threat potential. In this connection, when analyzing the contents, to take into account the influence of the material of which the container is composed. The inventor has realized that containers usually feature symmetry properties. The inventor therefore proposes using this prior knowledge for discovering containers in an X-ray image.

Containers that are found in pieces of luggage are often bottles. For this reason, in the following explanations, a "bottle" is used as a synonym for the class "container with at least one symmetry property;" this does not, however, mean that the principles explained here are limited exclusively to bottles. Basically, the methods and improvements proposed by the inventor can be correspondingly used, for example, to detect pipe bombs, parts of weapons or ammunition, or the like. The expression "at least one symmetry property" means that the container does not necessarily have to have a symmetrical shape from all possible viewing angles and/or can be symmetrical only in subregions. A symmetry property of an item is defined by an associated symmetry line. If the symmetry lines belonging to items in an image are known, then the item contained in the image is easier to discover or detect in that in the image, the image regions belonging to such an item can be more easily identified and segmented. The inventor proposes using this on X-ray images.

To prepare for the discovery of symmetry lines, an X-ray image is first preprocessed in order to identify features in the X-ray image. In this connection, the features to be identified in the X-ray image can be associated with a direction. The result of this preprocessing of the X-ray image is then a feature image, in which the identified features are highlighted and/or masked out. Outer edges of individual items contained in the X-ray image may be detected as features. The result of the preprocessing of the X-ray image is then an edge image, in which the outer edges that have been identified as features are highlighted and/or masked out (i.e. picture elements, that probably do not belong to an outer edge have been filtered out). This preprocessing can also be referred to as edge extraction.

In this context, however, it is not yet known which edges in such an edge image belong to a particular item. The association of particular outer edges with a particular item more or less constitutes the discovery of the item. This is a decisive difference relative to the method known in the prior art in which items already detected in an image are to be ascertained in greater detail, for example by inspecting the already known outer edges of such an item for symmetry properties. The present disclosure (as explained in greater detail below) is based on a different approach in that according to the core concept of the present disclosure, the attempt is made to discover a symmetry line in the edge image, which could belong to an item with symmetry properties. Based on a discovered symmetry line, it is possible to identify the outer edges of an item belonging to this symmetry line and it is thus possible to discover the item in the image.

In this context, the "outer edges" or "outer edge" of an item are understood to be definable lines in the X-ray image, which is/are a part of an outline or the entire outline of the item appearing in the X-ray image. The outline of the item in the X-ray image corresponds to the silhouette of the item from the respective viewing direction. The viewing direction in this case corresponds to the irradiation direction of the inspection object when the X-ray image is produced.

Functionally speaking, in edge determination, flat regions in the X-ray image, which differ sufficiently in their color value or gray value and/or brightness and/or intensity, are distinguished from one another. The line or lines between these distinguishable regions constitutes an edge of the edge image to be produced. From image processing, special edge detection algorithms are known, which make it possible to identify transitions between such distinguishable regions and to identify them as edges. Based on an X-ray image, an edge detection algorithm calculates the associated edge image. In this case, for example, each picture element of the X-ray image is reset through discrete convolution a correspondingly established filter matrix; the filter matrix is often also referred to as the operator of the associated filter algorithm. The chief difference among the various edge filters essentially lies in differently adapted filter matrixes; it is also possible to use a plurality of different filter matrixes.

To find edges in the X-ray image, it is possible, for example, to use an image processing filter like the image processing algorithm known as a Canny filter. The Canny filter is described by John Francis Canny in "A Computational Approach to Edge Detection," IEEE Transactions on Pattern Analysis and Machine Intelligence, Vol. PAMI-8, No. 6, November 1986. According to the use context proposed here, the Canny filter can be used on an X-ray image as a digitized image. Naturally, it is also possible to use other known or future image processing algorithms that are suitable for detecting edges in an X-ray image. In other words, in order to create an edge image from an X-ray image, it is possible to use one or a combination of the following known edge operators: a Sobel operator, a Scharr operator, a Laplace operator, a Prewitt operator, a Roberts operator, a Kirsch operator, and a Marr-Hildreth operator.

An outer edge identified as a feature can be associated with a direction. The direction can be defined as the direction vector of a tangent to the outer edge at a respectively considered edge picture element. In other words, the associated direction then corresponds essentially to an orientation of the edge in the edge picture element in question or to an orientation of an edge section of the outer edge. The direction thus ascertained may be determined taking into account an orbital direction defined for items contained in the X-ray image, for example, in such a way that based on the direction vector, it is always possible to clearly determine the side of the direction vector (left or right) on which the item to which the outer edge belongs lies. In some embodiments, the direction can be defined in such a way that the direction points out from the associated item or into the item; mathematically, this direction definition corresponds to the normal to the corresponding tangent at the edge picture element of the outer edge under consideration.

Prior knowledge about edges of particular items in X-ray images may be used in order to eliminate edges of items that are not of interest from the edge image before further image processing. To that end, it is possible, for example, to analyze distinctive points and/or their surrounding region in the vicinity of discovered edges in the X-ray image. The analysis results are suitable for determining whether or not a discovered edge belongs to a container. To that end, it is possible, for example in an X-ray image, to determine feature descriptors in image regions of the identified edges for selected picture elements, which descriptors are suitable for validating edges identified in the X-ray image as outer edges of containers. It is thus possible for those edges in the edge image that are probably not outer edges of containers to be eliminated before the determination of symmetry lines. For example, in an X-ray image, the "scale-invariant feature transform (SIFT) can determine feature descriptors for image regions for or around selected key (picture) elements. The SIFT is an algorithm for extracting local image features from images, which was published by David G. Lowe at the University of British Columbia in 1999 and is described, among other things, in U.S. Pat. No. 6,711,293 B1 or in David G. Lowe, "Distinctive Image Features from Scale-Invariant Keypoints," International Journal of Computer Vision, 2004. The SIFT algorithm can be used on a digitized image in the form of an X-ray image. The person skilled in the art of image processing is able to adapt the SIFT algorithm for the above-described validation or recognition of outer edges of containers in X-ray images, for example as described below.

The edges that are known based on the edge image define objects whose properties differ from their environment and which are not sensitive to perspective distortion. The SIFT algorithm can thus be used to determine feature descriptors for image regions of the X-ray image in the vicinity of edge picture elements. For example, such image regions can be characterized by means of direction histograms, whose features can be stored in vectors. The vectors thus determined can serve as a finger-print, so to speak, for comparison with reference data. The reference data can, for example, be determined with X-ray images of known items, in particular containers. In other words, the SIFT features can be used as descriptors for the purpose of detecting outer edges of a container. The detected SIFT features are suitable, for example, as an index of edge models with similar features. In other words, the edges determined in the X-ray image can, based on the determined SIFT features, be validated through comparison with known edge models for container edges in X-ray images. In other words, a SIFT feature determined in the X-ray image for a key (picture) element of an edge can be compared to known features in a database of container outer edges. When there is sufficient agreement or similarity, it can be concluded that the determined edge is an outer edge of a container.

For the comparison with references, it is possible for example to use the RANSAC algorithm (random sample consensus, which roughly translates to "agreement with a random sample"), which is particularly suitable for estimating a model within a series of measurement values that includes outliers and blatant errors.

The features extracted by means of SIFT may be insensitive to coordinate transformations such as translation, rotation, and scaling. The features are also robust in the presence of lighting variations, image noise, and reduced higher-order geometric deformation of the kind that occurs, for example, when performing projective imaging of an item from different points of view.

Based on the edge image produced from the X-ray image, it is possible to detect pairs of edge picture elements of the symmetry lines that can be associated with the edges.

When evaluating the identified edges in the edge image, it may occur that a symmetry line is incorrectly detected which does actually match edges of items contained in the X-ray image, but these edges do not belong to the same item, instead belonging to different items. Such symmetry lines are referred to herein as pseudo-symmetry lines. The detection of pseudo-symmetry lines may be avoided as much as possible. Among others, this is one aspect of the improvements proposed herein.

Based on a recognized symmetry line, it is possible to detect the associated item in the X-ray image. An associated symmetrical region of the item is segmented for this purpose.

In order to detect symmetry lines in the edge image produced from the X-ray image, it is possible, for example, to use an image processing algorithm, as proposed by Li, Zhang, and Kleeman in "Real Time Detection and Segmentation of Reflectionally Symmetric Objects in Digital Images," Proceedings of the 2006 IEEE/RSJ, International Conference on Intelligent Robots and Systems, Oct. 9-15, 2006, Beijing, China. In order to avoid repetitions, the contents of this publication are incorporated into the present document by reference; this relates in particular to the statements with regard to basic principles and functionalities of the algorithms described therein for detecting symmetry lines in an edge image, with regard to the construction of an outline of an item belonging to a detected symmetry line, and with regard to the segmentation of symmetrical edges that can be associated with the detected symmetry lines and thus of symmetrical regions in the edge image that are defined by the respective edges and can be associated with items having symmetry properties in the original X-ray image.

The symmetrical regions of the X-ray image that are segmented in the edge image can be subjected to further analyses based on other information that is known about the individual picture elements, such as material properties.

An item identified in different X-ray image views cannot be validated based on the identified outer edges since the image regions belonging to the item are usually not similar. The inventor, however, has discovered that the item can be validated in the 3D space by means of the symmetry lines identified in the individual X-ray images. A symmetry line in an X-ray image is initially not uniquely defined in the 3D space but instead corresponds to a symmetry plane in the 3D space. If symmetry lines of the same item have been detected in at least three different X-ray image views, then it is possible for the symmetry planes of these symmetry lines to be projected into the three-dimensional (3D) space. If the same item has in fact been detected in all of the X-ray images, then theoretically, all of the intersecting lines of two respective symmetry planes in the 3D space lie in the same region, i.e. adjacent to one another. In practice, the intersecting lines lie adjacent to each other at least within a particular tolerance range and at least are oriented in the same direction. The associated item can therefore be validated in the 3D space by means of the determined symmetry line.

In addition to using the above-mentioned algorithms or functionally similar ones on X-ray images, the inventor particularly proposes additional measures, particularly in order to improve the segmentation of the items having symmetry properties contained in the X-ray image. The additional measures achieve the fact that the method—or a computer program that executes the method—functions more robustly and/or quickly.

A first aspect of the present disclosure therefore relates to a method for detecting an item with symmetry properties inside an inspection object based on at least one X-ray image. As explained above, the method is suitable for detecting containers that can contain liquids, for example bottles, in inspection objects in the form of pieces of luggage.

The method may include the following steps: (a) detection of edges of items contained in the X-ray image in order to produce an edge image; and (b) detection of the item by searching for a symmetry line that can be associated with an item with symmetry properties contained in the X-ray image based on pairs of edge picture elements of the edge image that are symmetrical to each other relative to the symmetry line. In step (b), when determining the symmetry line in the edge image, the only edge picture elements taken into account are those in relation to which a symmetry line of an item to which the edge belongs lies in an image region of the X-ray image that can be associated with the item.

The inventor has discovered that based on intensity values for X-rays not absorbed by the inspection object measured for individual picture elements in the X-ray image, it is possible to determine which side of an edge under consideration is the one on which an image region of the X-ray image constitutes part of the item associated with the edge. Unlike in conventional photographs, at edges of items in X-ray images, it is possible to identify which side of the edge is the one on which an image region is part of an item. X-ray images are transmission images. Thus due to the absorption of X-rays by the item, regions of the X-ray image that are part of an item are darker than the image region surrounding the item. In other words, in these locations, lower intensities are measured in the detected X-rays due to the absorption of X-rays by the item. In the present context, this prior knowledge is used in that when determining a symmetry line, an edge in the edge image is only taken into account if, viewed from the edge, the symmetry line actually lies within the item, i.e. within the darker image region to which the edge under consideration belongs.

From a practical standpoint, this can be implemented in the algorithm for discovering a symmetry line in that for edges and/or edge picture elements, based on intensity information that is known for the individual picture elements of the X-ray image, a direction vector is determined and stored for the respective edge and/or the respective edge picture element.

The direction vector can be defined so that starting from an edge or an edge picture element, it points in direction of the image region in which the item to which the edge belongs lies. When determining a symmetry line, the respective direction vector of an edge or edge picture element can be used as a criterion for whether the edge picture element belongs to a particular symmetry line or not. According to the direction vector definition proposed as an example, this means that when determining a symmetry line, edges and/or edge picture elements are only taken into account if their direction vectors point or are oriented toward this symmetry line.

The improvement explained above makes it possible to cut the detection of pseudo-symmetry lines in half.

A use of the method in a dual-energy or multiple-energy X-ray inspection system, as is known for example from DE 101 49 254 A1, makes it possible to modify the method in that in step (a), the edge image is produced based on individual picture elements of the material information associated with the X-ray image. It is thus possible to search for items made of different materials such as plastic and glass in separate searches. In other words, it is thus possible to search X-ray images separately for bottles made of different materials such as glass or plastic. For example, in X-ray images that have been produced by means of a two-energy or dual-energy X-ray method, individual picture elements (pixels) of the X-ray image can be differentiated according to an effective atomic number ($Z_{eff}$) of the irradiated material that has been established for this location. Typically, the $Z_{eff}$ for glass lies in the range from 12 to 13 and for plastics, lies in the range from 6 to 7.

Before a further processing of the edge image, the edges identified in it can be validated as to whether they are actually outer edges of items. To this end, it is possible, for example, to determine at least one feature descriptor, for example, for at least one image region in the vicinity of a selected edge picture element in the transmission image. The at least one feature descriptor can, for example, be determined based on the above-described scale-invariant feature transform (SIFT) of the image region. Then the at least one feature descriptor can be compared to previously known reference values. It is thus possible to validate the selected edge picture element as an outer edge of a container. For example, it is possible for those edges in the edge image that are probably not outer edges of containers to be deleted or correspondingly weighted. Such edges are then no longer taken into account in the subsequent determination of symmetry lines.

In order to identify possible symmetry lines in the edge image, it is possible, as in the algorithm of Li, Zhang, and Kleeman, to rotate the edge image incrementally over a predetermined angular range from 0 to π (0 to 180°) in order to identify a symmetry line in the rotated edge image, which extends at the respective rotation angle Θ relative to one of the outer edges of the image. In other words, a search is carried out for a respective vertically extending symmetry line in the rotated image. To that end, in step (b), the edge image is rotated through the predetermined angular range incrementally, such as in equidistant steps. In the rotated edge image, based on a symmetry property of an item, symmetry lines are correspondingly determined for edges or edge picture elements that are symmetrical to each other.

According to one or more modifications, for each rotation angle Θ, it is proposed to not take into account, i.e. to not use for the determination of a symmetry line, those edge picture elements that belong to an edge in the rotated edge image that extends orthogonal or approximately orthogonal to a symmetry line. This likewise reduces the detection of pseudo-symmetry lines and also reduces the computation effort required by the algorithm.

Particularly when the items to be detected are bottles, they very often have an outline that is largely composed of rectilinear edge sections from almost every viewing direction. The method for detecting a symmetry line can thus be improved in that for each nearly rectilinear edge in the edge image, an edge direction vector is determined and the associated edge is saved in memory for the associated edge picture elements. In some embodiments, when determining a symmetry line, the only edge picture elements that are taken into account are those edge pairs that extend symmetrically to each other relative to this symmetry line. In other words, by means of the edge direction vectors stored in memory for the edge picture elements, it is possible to carry out a plausibility test for an edge picture element pair possibly positioned symmetrical relative to a symmetry line under consideration. If the test shows that the edge direction vectors under consideration do not extend symmetrically to each other relative to the supposed symmetry line, then these edge picture elements are not taken into account in the determination of the symmetry line under consideration.

The edge direction vector and the above-mentioned direction vector for identifying the image region belonging to an item are orthogonal to each other. In other words, the direction information contained in the two vectors is redundant. It can therefore be sufficient to determine and store in memory only one of the two vectors.

According to the method for detecting symmetrical items in digital images proposed by Li, Zhang, and Kleeman, an item with symmetry properties in the edge image can be segmented based on the associated symmetry line by determining an outline for the item. Since it is known that a detected symmetry line belongs to an item with a symmetry property, it is possible to determine as an outline a contour line that is symmetrical to the detected symmetry line. The outline distinguishes the item from its surroundings. The outline can be determined based on the edges that are associated with the same symmetry line.

In order to identify edge picture elements that are probably outline picture elements, it is possible to weight edge picture elements that are symmetrical to each other with regard to the symmetry line. The weighting can be carried out taking into account a respective distance between two edge line points that can be associated with each other relative to the symmetry line and a distance of the center point of a connecting line of the two edge line points from the symmetry line. Based on the edge picture elements that are thus evaluated with weightings, it is finally possible in a retracing method to construct the outline, taking into account the respective weights associated with the edge picture elements.

Particularly in X-ray images of pieces of luggage, which contain many items jumbled together, items can overlap in the X-ray image. This results in the fact that edges and regions of items partially transition into one another in the X-ray image and are thus difficult to distinguish from one another. It is particularly problematic in this context that when there are overlaps in the X-ray image, the outline of individual items, particularly those made of similar materials, can no longer be identified by a high contrast difference. In the associated edge images, therefore, the overlapping items lack outer edges in the overlap region.

In one or more modifications, the method according to the present disclosure therefore also has a step (c) for segmenting an item with symmetry properties in the edge image based on the associated symmetry line; an outline for the item is determined, which distinguishes the item from its surroundings. In step (c), in two edges that have been determined to be symmetrical to a symmetry line, edge picture elements that are missing from one of the edges may be added to the respective other edge in mirror-symmetrical fashion relative to the symmetry line by taking into account the respective other edge. In other words, the gap is filled in mirror-symmetrical fashion relative to the symmetry line, in accordance with the shape of the other edge. It is thus possible to close gaps in edges of the outline that lie in an overlap region.

The overlap region, in which the item and the edge of the item are partially overlapped by another item, can be determined based on picture elements that belong to the overlap region. Overlap regions in X-ray images are distinguished by the fact that lower intensity values for X-rays are measured there than in the image regions of the individual items without the overlap. In other words, in X-ray images, overlap regions are likewise darker than non-overlapping regions. Also in X-ray images, it is not important that the overlapping item be situated in front of the covered item; it can also lie behind it. This results in the same depiction in the X-ray image.

This measure enables improved segmentation of items with a symmetry property that are partially covered.

In another modification of the method, a respective symmetry line for a particular item with symmetry properties is determined in at least three X-ray images of the same inspection object from different respective irradiation directions. The method can then also have: (d) projection of the detected symmetry lines of the individual X-ray images as symmetry planes into a three-dimensional (3D) space by means of a projection into a 3D space and testing of the position of intersecting lines of the symmetry planes relative to one another in the 3D space. In other words, the symmetry property of the item can be validated by means of the detected symmetry lines. To that end, a check is performed as to whether the intersecting lines of the symmetry planes in the 3D space have approximately the same direction and are adjacent to one another within a particular tolerance range, for example in the image region of the item. In other words, a check is performed as to whether or not the intersecting lines are approximately parallel to one another and are spaced apart by a distance that does not exceed a predetermined value.

The method is particularly suitable for detecting bottles as the item with symmetry properties, for example in a piece of luggage as an inspection object. When bottles are detected in an X-ray image, it is therefore possible to first search the X-ray image for symmetry lines that can be associated with a bottle. If a symmetry line has been detected, it is then possible to segment a symmetrical region in the X-ray image that belongs to the bottle. If several X-ray images of the same object from different viewing directions are available, then the symmetry lines and thus the bottle can be validated in the three-dimensional space.

In a modification, in a step (e) of the method, a bottom of the bottle and a neck of the bottle are determined in the respective X-ray images. This is possible in bottles, for example, because the bottom is usually wider than the bottle neck. In other words, it is possible to recognize the wide bottom and the neck that is thin in comparison to the bottom. By detecting the bottom of the bottle and the neck of the bottle, it is possible to uniquely associate the symmetry line of the bottle with one direction. This direction information can also be used in the validation of the symmetry line in the 3D space.

In another modification, the method according to the present disclosure has a step (f), in which an inference about the contents of an item with symmetry properties is drawn, taking into account the outer material of the item. As explained above, an X-ray inspection using X-rays of two energy levels or a corresponding evaluation of the transmission spectrum according to two different energy levels makes it possible to determine an assignable value of the effective atomic number for each picture element.

A second aspect of the present disclosure relates to a computer system as an image processing device with at least one processor, which is configured to execute one of the above-described methods for detecting an item with at least one symmetry property inside an inspection object based on at least one X-ray image or a plurality of X-ray images of the inspection object according to one of the preceding methods.

A third aspect of the present disclosure relates to an X-ray inspection system with a transport device that travels through an irradiation tunnel and with X-radiation sources arrayed around the transport device, which emit X-radiation in at least two different irradiation planes, each of which is associated with a respective detector array, and the X-ray inspection system has a computer system as described above or is operatively connected to such a computer system.

Another aspect of the present disclosure relates to a computer program or computer program product with program code for executing one of the above-described methods according to the present disclosure when the computer program is executed in a computer system. In other words, the present disclosure relates to a software means for implementing one of the above-described methods on a computer system. Another aspect of the present disclosure relates to a data storage device on which an electronically readable program code of the above-mentioned computer program is stored. In other words, the present disclosure also relates to a data storage device on which the software means for implementing one of the above-described methods on a computer system is stored. Another aspect of the present disclosure relates to a data stream that includes the program code of the above-mentioned computer program. In other words, the present disclosure also relates to software means in a form that can be transmitted between computer systems in a wired or wireless fashion.

With regard to the computer program, the data storage device, and the data stream, it should be noted that the computer system for implementing the image processing device may be a conventional computer such as a workstation or a laptop, which is or can be operatively connected to an X-ray inspection system or can be a computer system that is specialized in image processing and can be integrated into an X-ray inspection system.

The computer and the arithmetic unit are equipped in a known way either with a standard operating system as a programming environment for the execution of computer programs or with a proprietary programming environment for a programming code or software means that is especially adapted thereto. The computer system can have a non-erasable storage (read-only memory) for basic programming functions of the system and a volatile memory (read/write memory) for programming code of a computer program that is loaded into the system and/or can have working data that is required or produced during execution of the computer program. The programming code of a computer program loaded into the system can also be stored on a read only memory. The computer system can also include at least one programmable arithmetic unit such as one or more microprocessor(s) or the like. The programmable arithmetic unit executes instructions of a computer program that are programmed by means of the programming code in order to implement a method that is programmed by means of the computer program, e.g. one of the methods described herein. The computer system can also have interfaces for inputting and outputting data. This particularly includes the possibility of being able to load programming code into the computer system from a data storage device or in the form of a data stream from a computer network such as a local computer network, the Internet, or the like.

The present disclosure is particularly suitable for use in image processing devices in—or in connection with—an X-ray inspection system of the kind used in security check stations for security screening of airline passengers or in the luggage handling system, for example at airports. In this case, pieces of luggage and/or freight goods as inspection objects that are to be loaded on board an aircraft undergo automatic nondestructive inspection. Such X-ray inspection systems can also be used at other checkpoints e.g. at entrances to security-relevant areas or buildings, at border checkpoints, etc. for inspecting objects such as hand luggage carried by people or postal items such as letters, packages, or parcels. The goal of such inspections can be to detect particular items such as data storage devices, e.g. DVDs or CD-ROMs, or substances such as drugs, but also to detect materials and substances with hazard potential such as explosives or chemicals. The above items can themselves have symmetry properties or the above items, materials, and substances can also be concealed in containers that have symmetry properties.

Other advantages, features, and details of the present disclosure ensue from the following description, in which exemplary embodiments of the present disclosure are described in detail with reference to the drawings. Features mentioned in the claims and in the description can be essential to the present disclosure by themselves or in any combination with one another. Likewise, the features mentioned above and described in greater detail here can each be used alone or several at a time in any combination. Functionally similar or identical parts or components are sometimes provided with the same reference numerals. The terms "left," "right," "top," and "bottom" used in the description of the exemplary embodiments relate to the drawings in an orientation in which a figure name and/or reference numerals can be read in the normal way. The embodiments shown and described are understood to be non-exhaustive and are merely exemplary in character in order to explain the present disclosure. The detailed description is provided for the information of the person skilled in the art; for this reason, known circuits, structures, and methods are not shown or explained in detail in the description in order not to interfere with the comprehension of the present disclosure.

DETAILED DESCRIPTION

It should be noted that the illustrations in FIGS. 1, 3, 6, and 7 through 8 have been adapted by means of a Floyd-Steinberg dithering algorithm to enable black and white reproduction, i.e. they are schematic depictions of X-ray images provided for explanatory purposes.

The terms "coupled" and "connected/attached" and terms derived from them are not used synonymously herein. "Connected/attached" means that two or more elements are in direct physical or electrical contact with one another. "Coupled" means that two or more elements cooperate or influence one another; they can be in direct or also indirect physical or electrical contact with one another. Unless otherwise indicated, the use of the ordinal adjectives "first," "second," "third," etc. to indicate a common object merely indicates that reference is being made to different examples of similar objects, and should not be taken to imply that thus-designated objects must occur in a certain chronological, spatial, priority-ranked, or other sequence.

Figure 1:
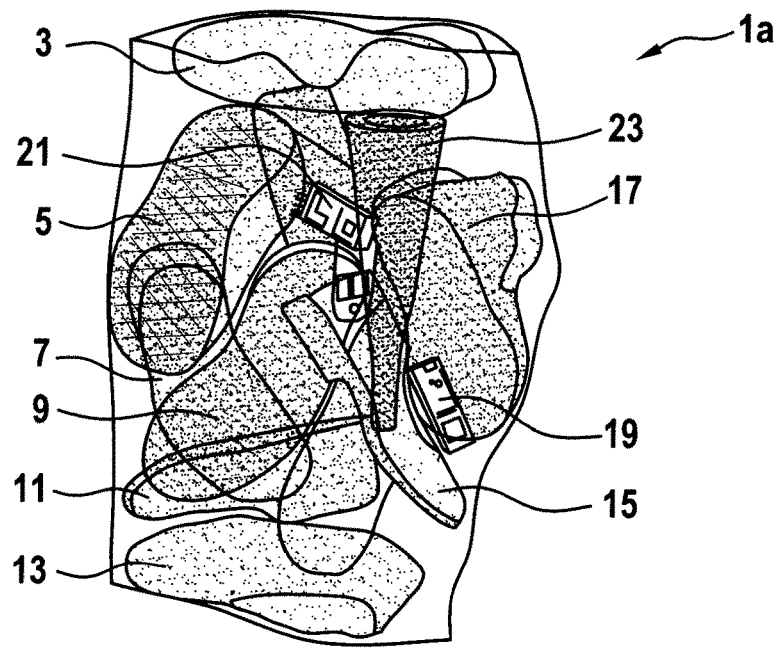
FIGS. 1 and 2 show a first example of an X-ray image of a first piece of luggage and an associated edge image.

FIG. 1 shows an example of an X-ray image 1*a* of a first piece of luggage in the form of a bag. The X-ray image 1*a* shows individual items that can be easily recognized and identified by the human observer. Thus in the first piece of luggage irradiated with X-rays, it is possible to recognize, among other things, several shoes 3, 5, 7, 9, 11, 13, 15, 17 and electronic devices 19, 21. The items also include a bottle 23.

As mentioned at the beginning, bottles in particular constitute a hazard risk in security-relevant areas because they can contain undeclared substances such as liquids, gels, creams, etc. For this reason, bringing substances in the form of liquids, gels, or creams in hand luggage on board an aircraft is now severely restricted or prohibited. It is therefore necessary to be able to reliably detect such containers in security checks.

An X-ray inspection system of the kind usually used for baggage screening at airports shows one or more X-ray images of an inspection object such as a piece of hand luggage on a display unit. Security personnel that are present must then be able to quickly and reliably recognize from the X-ray image(s) whether a security-relevant item is contain therein. The X-ray inspection system may be able to automatically analyze and evaluate security-critical items in pieces of luggage, for example containers, in particular bottles, as to the potential security risk they pose. A container that has been classified as harmless can then be correspondingly designated so that the operator recognizes that it does not require further inspection, in particular further time-consuming manual visual inspection.

Figure 2:
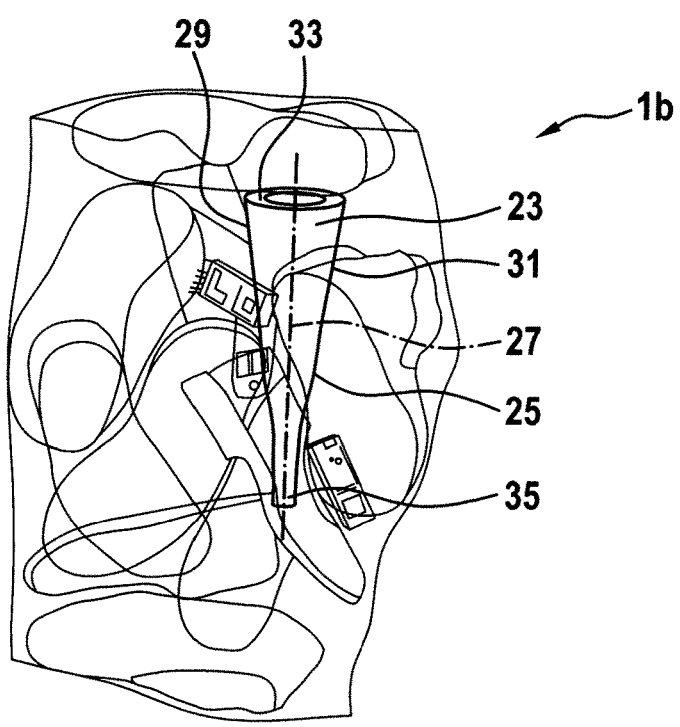

FIG. 2 shows an edge image 1*b* produced based on the X-ray image in FIG. 1. The edge image 1*b* has been produced by means of an algorithm for detecting edges in an image, such as the Canny filter mentioned at the beginning. In this case, based on known material information for individual picture elements such as the effective atomic number ($Z_{\textit{eff}}$), the edge search can be additionally limited to items made of glass. It should be noted that other material information for individual picture elements—if known—can also be taken into account; this can, for example, be a mass attenuation coefficient and/or the specific density. Alternatively or additionally, other features that are suitable can be used for identification, such as the outer edges of containers, in particular bottles. For example, the SIFT algorithm discussed at the beginning can be used in the X-ray image to determine feature descriptors in the image area of distinctive picture elements. For example, at selected edge picture elements of identified edges, the surroundings can be detected in a scale- and rotation-invariant form. Based on the SIFT features detected in this way, the edge identified in the X-ray image can be validated through comparison to known edge models for container edges in X-ray images. If it is determined here that it can be inferred with a certain probability that the associated edge in the edge image is not an outer edge of a container, then it can be deleted or left out of consideration in further analyses.

In edge image 1b, which is shown in FIG. 2, an outline 25 of the bottle 23 is easily recognizable to the human observer. For a machine, the problem is to recognize that the edges that form the outline 25 belong to one item so as to be able to perform the segmentation of this item.

According to the solution proposed here, certain items can be better identified based on symmetry properties. The bottle 23, for example, features symmetry properties with regard to a symmetry line 27 that may be detected.

The outline 25 of the bottle 23 has two side edges 29 and 31 extending symmetrically to each other. Consequently, these side edges 29, 31 can easily be associated with the bottle 23 if the symmetry line 27 is known. A bottom 33 of the bottle 23 and a neck 35 of the bottle are visible. The bottom 33 of the bottle 23 is typically wider than the neck 35 of the bottle 23.

Figure 3:
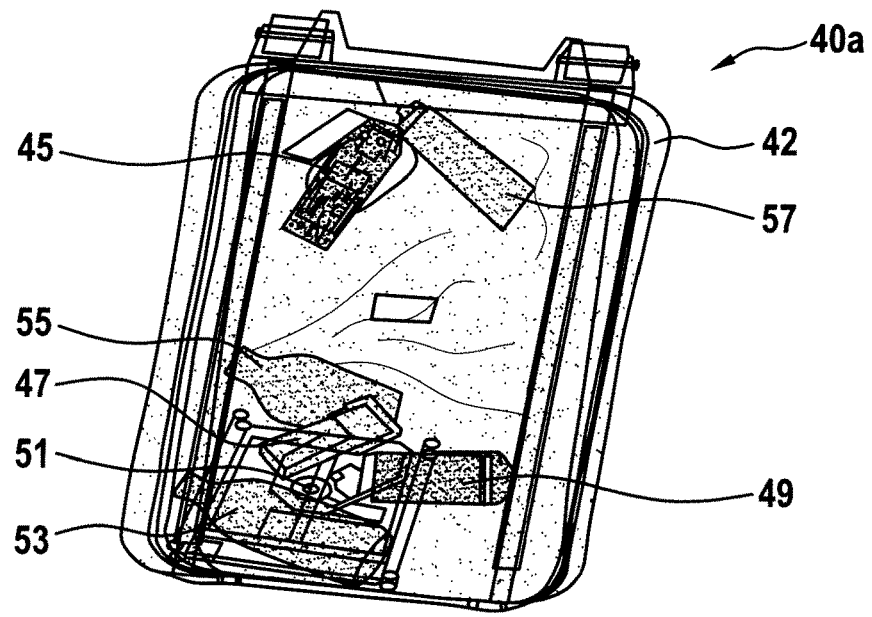
FIGS. 3 and 4 show a second example of an X-ray image of a first piece of luggage and an associated edge image.

FIG. 3 shows another example of an X-ray image 40a of a second piece of luggage 42, which is a suitcase. Once again, the X-ray image 40a contains individual items that are recognizable to the human observer. For example, the second X-rayed piece of luggage 42 contains a plurality of electronic devices 45, 47, 49, and 51, among other things. The items also include bottles 53, 55, and 57.

Figure 4:
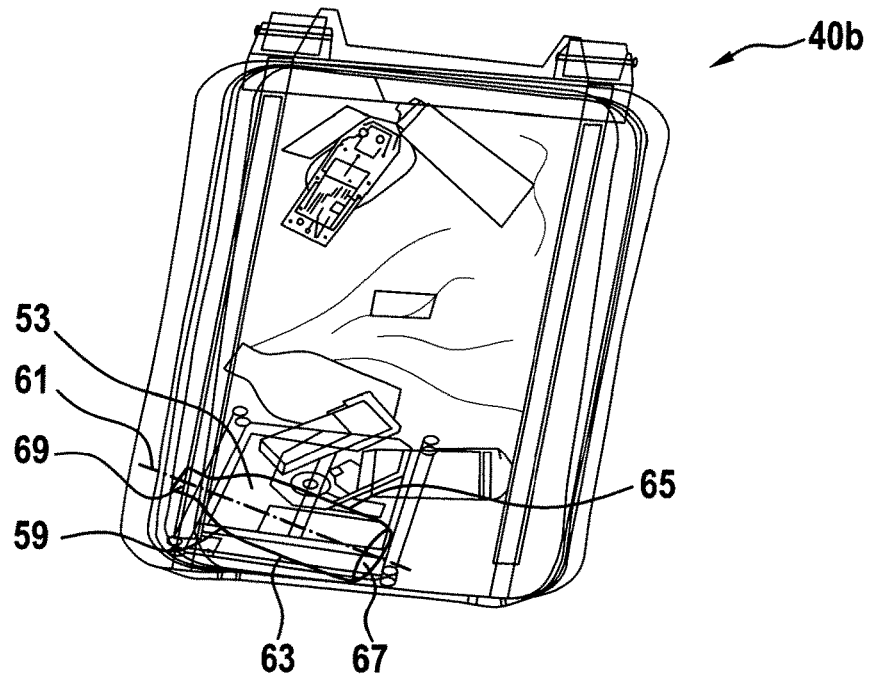

FIG. 4 shows an edge image 40b. The edge image 40b was produced by means of a Canny filter. As in FIG. 2, the edge search has been limited to items made of glass, based on material information for the individual picture elements.

In the edge image 40b in FIG. 4, an outline 59 of the bottle 53 is clearly recognizable to the human observer. As in the example in FIGS. 1 and 2, the bottle 53 is characterized by symmetry properties relative to a symmetry line 61 that may be detected. The outline 59 of the bottle 53 has two side edges 63 and 65 extending symmetrical to each other. A wide bottom 67 of the bottle 53 and a narrow neck 69 of the bottle 53 are also visible.

Figure 5:
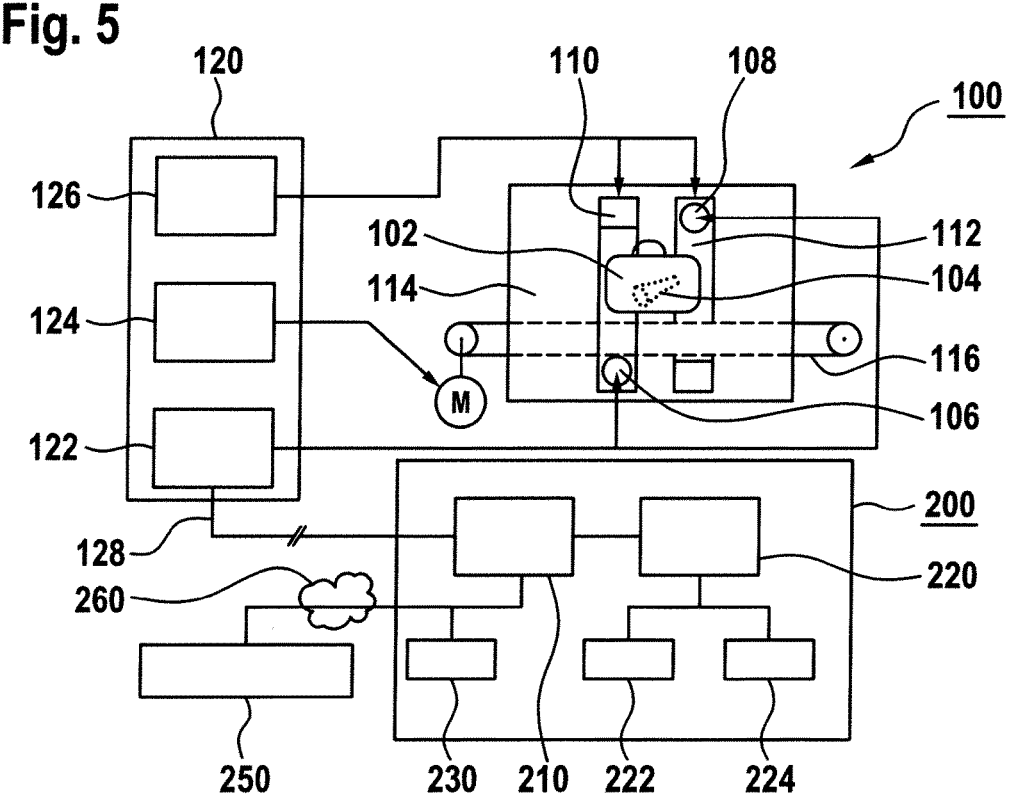
FIG. 5 shows a schematic block diagram of an X-ray inspection system with an image processing device for executing the proposed method for detecting items with symmetry properties in X-ray images.
Figure 6:
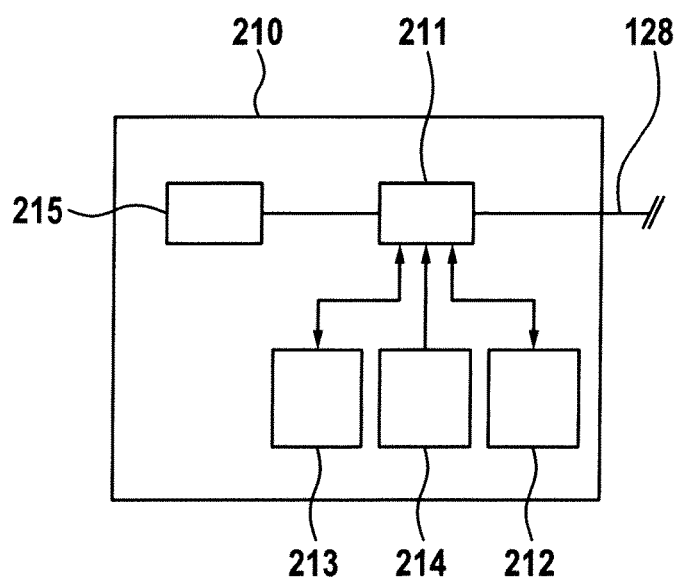
FIG. 6 shows a schematic block diagram of the image processing device of the X-ray inspection system in FIG. 5.

Before discussing the individual measures proposed for improving the detection of items with symmetry properties in X-ray images, an X-ray inspection system 100 should be briefly explained in conjunction with FIG. 5. The X-ray inspection system 100 can produce X-ray images of inspection objects, which images are to be processed. FIG. 6 shows a schematic block diagram of an image processing device 210, which can be part of the X-ray inspection system in FIG. 5 or can alternatively be operatively coupled to it. For example, the image processing device 210 can be coupled via a wired or wireless data connection and can be configured by programming to execute one of the methods proposed herein.

FIG. 5 schematically depicts an inspection device in the form of the X-ray inspection system 100, which is used for security screening of inspection objects 102 such as pieces of luggage from the images in FIGS. 1 through 4. Such inspections are usually performed at airports. The goal is to identify articles 104 contained in pieces of luggage in order to evaluate them with regard to their potential security risk and if advisable, to inspect them more closely. By means of method proposed here for detecting items with symmetry properties in X-ray images, the X-ray inspection system 100 is improved with regard to the detection of bottles in pieces of luggage.

The schematically depicted X-ray inspection system 100 in FIG. 5 essentially contains a plurality of stationary X-ray tube assemblies 106 and 108 as radiation sources and associated detector arrays 110 and 112. The detector arrays 110 and 112 are configured to measure the intensities of unabsorbed X-rays. The radiation sources emit X-rays in an energy range of up to a maximum of 160 keV. For the sake of simplicity, only two radiation sources and their associated L-shaped linear scanners as detector units are shown in FIG. 5.

The X-ray tube assemblies 106 and 108 are arranged so that the inspection object 102 is irradiated in different respective directions. As a result, mutually independent data about the object 102 are obtained. To that end, the X-ray tube assemblies 106 and 108 are spaced apart from each other in the transport direction of the object 102 at different locations lateral to an irradiation tunnel 114. The object 102 is transported through the irradiation tunnel 114 by a transport apparatus, such as a belt conveyor 116. Naturally, more than the two X-ray tube assemblies 106 and 108 and correspondingly more than the two detector arrays 110 and 112, as shown for example in DE 101 49 254 A1, can be provided to produce more than two X-ray images from different viewing directions, i.e. different views of the object to be inspected (inspection object) 102.

In the sample X-ray inspection system 100 shown in FIG. 5, the X-ray tube assemblies 106 and 108 each emit X-rays in two, for example, fan-shaped irradiation planes in order to irradiate the inspection object 102. A respective detector array 110 and 112 is oriented in each of the irradiation planes. The object 102 is thus irradiated in at least two separate irradiation planes that are oriented parallel to each other. It is basically also possible for the irradiation planes to not be oriented parallel to each other. In any case, the respective directions in which the inspection object 102 is irradiated are known and can be taken into account in analyses evaluating the information about the two X-ray images detected by the detector arrays 110 and 112.

The detector arrays 110 and 112 contain respective detectors in a line-shaped array, which may be L-shaped, for example. It is thus possible to detect all of the rays passing through the object 102 while requiring only a small amount of space for the detector arrays. The detector arrays 110 and 112 contain double detectors that are configured to use a basically known multiple-energy or dual-energy method to measure the intensities of X-rays separately according to high and low energies.

The X-ray inspection system 100 also has a control unit 120 that is operatively coupled to an evaluation unit 200. The control unit 120 includes an X-ray control unit 122 that is operatively coupled to the X-ray tube assemblies 106 and 108 and is configured to control them. The control unit 120 also includes a transport control unit 124 that is operatively coupled to the belt conveyor 116 serving as a transport apparatus and may be configured to control the latter to transport the object 102 smoothly through the X-ray inspection system 100. The control unit 120 also includes a detector data acquisition unit 126 that is operatively coupled to the detector arrays 110 and 112 and is configured to receive the intensity values of X-rays that have passed through the object 102 and been measured by the detector arrays 110 and 112. The control unit 120 itself coordinates the control tasks of the units 122, 124, and 126 and via a data connection 128, supplies the intensity data received from the detector data acquisition unit 126 to an evaluation unit 200 for further processing.

The evaluation unit 200 has an image processing device 210 and an imaging unit 220 with a screen 222 and, where necessary, a printer 224, by means of which the X-ray images of the object 102 and the items 104 contained therein—which images are produced based on the detected intensity values—are displayed for the visual inspection by an operator.

A database 230 coupled to the image processing device 210 stores, for example, values of at least one specific variable that influences the absorption of X-rays by various materials so that it is possible to detect the presence of the latter. Materials of this kind are in particular substances and materials with threat potential, whose presence in the object 102 must be detected, particular as the contents of items 104 concealed in the object 102, as well as materials of which such an item can be composed.

Liquids are predominantly stored in bottle-like containers. Since the material of the container encloses a potentially dangerous liquid, it makes it harder to evaluate liquid contained in an X-ray image. In the image evaluation, an item may be identified as a bottle so that it is possible in the evaluation of the contents of the bottle, to take into account the influence of the material of the bottle.

In order to detect a particular material such as glass in the object 102, the latter is conveyed on the belt conveyor 116 through the different irradiation planes produced by the X-ray tube assemblies 106 and 108, with the intensities of the unabsorbed X-radiation being measured by the respective detector arrays 110 and 112. Based on the measured intensity values, each of the detector arrays 110 and 112 produces a respective two-dimensional X-ray image (see FIGS. 1 and 3) of the object 102, which is stored in the image processing unit 210 of the evaluation unit 200 for further processing.

An X-ray image can be composed of picture elements (pixels) with associated values for the intensity and/or color based on a material variable, which is determined on the basis of the intensities received by the respective detectors. For example, for each picture element, the value of the effective atomic number ($Z_{eff}$) is determined, which is determined according to a known dual-energy- or multiple-energy method based on respective intensity values for the high and low energy spectrum. The determined value can be displayed on the screen 222 as an associated gray value or color value. In the X-ray image, regions are then determined in which the value of the material variable—i.e. the value of $Z_{eff}$ in the example—lies within a range that is of interest, for example lies in a value range of plastic ($Z_{eff}$ of approximately 6 to 7) or glass ($Z_{eff}$ of approximately 13 to 14) as a typical material for bottles. Regions of the X-ray image that have been identified as belonging to a bottle and have been segmented constitute a spatial region and thus an item 104 inside the object 102, and are singled out for further inspection of the contents of the bottles.

FIG. 6 schematically depicts a simplified block circuit diagram of the image processing unit 210 in FIG. 5 for implementing one of the methods proposed herein for detecting items 104 with at least one symmetry property in the object 102.

It is understood that the evaluation unit 200 and the control unit 120 can also be implemented in the form of a system control by means of a single computer system.

It is also understood that the processing and evaluation of the intensity values detected by the inspection device 100 can take place in a computer system 250 that is situated locally in or on the X-ray inspection system 100. Naturally, it is also possible for such a computer system 250, for example coupled via a computer network 260, to be centrally positioned at a central location like a mainframe computer system, in particular for a plurality of X-ray inspection systems. It is also possible for the computer system 250 to be composed of a plurality of computer systems that are connected to one another via a computer network and are thus spatially distributed. It is also possible for the computer system 250 embodied in the form of a mobile computer to be connected to one or more X-ray inspection systems. Finally, the imaging unit 220 and the screen 222 can also be embodied as a mobile unit in the form of a tablet computer, which is particularly easy for inspection personnel to carry along with them and can be placed, for example, in a correct orientation next to a piece of luggage in order to be able to more easily detect an item to be inspected inside the piece of luggage.

FIG. 6 essentially shows only the basic components of the image processing unit 210 that are required to implement the evaluation of the detected X-ray images. The image processing unit 210 has at least one software-controllable processor 211. At least one first memory 212 stores software means, for example in the form of a computer program for implementing the desired functions/methods when the computer program is executed in the at least one processor 211.

At least one second memory 213 is provided as a working memory for data to be processed and for intermediate or final results. A third memory 214 can be provided, which stores, for example, the comparison values for specific material variable values instead of the database 230; these material variable values can, for example, be specific variables of known materials that influence the absorption of X-rays, in particular the density and/or mass attenuation coefficient and/or effective atomic number of these materials. It can also store, for example, model data as a reference for feature descriptors determined based on the X-ray image, e.g. for SIFT features.

The image processing unit 210 also has input means 215 such as a keyboard, a touchpad, a pointer input device (computer mouse), or the like and/or a variant of any one of these means specifically adapted for simple operation or a combination thereof.

The image processing unit 210 is coupled to the control unit 120 of the X-ray inspection system 100 via the data interface or data connection 128.

With regard to the image processing device 210, it should also be noted that the term "processor" can refer to any electronic unit and/or circuit or a part of an electronic unit or circuit, which process(es) electronic data from registers and/or from a memory in order to convert electronic data into other electronic data or to produce output data that correspond to input data and can be stored in registers and/or a memory. As stated above, the image processing unit 210 can include a processor 211 or a plurality of processors or processor cores.

In embodiments, the image processing unit 210 may be implemented as a combination of hard-ware, firmware, and software. Correspondingly, the methods described here can be partially or even completely composed of software means stored on a machine-readable medium, which can be read and executed in order to be carried out in the image processing unit 210. A machine-readable or electronically readable medium (data storage devices) can be configured for any mechanism for storing, transmitting, or receiving information in a form that can be read by a computer. Non-limiting examples of these include read-only memories (ROM), direct-access memories (RAM), magnetic storage discs, optical storage media, and flash storage media. Finally, the software means can also be configured in the form of a data stream such as signals transmitted optically, acoustically, or otherwise (e.g. carrier waves, infrared signals, digital signals, etc.), which can be transmitted via corresponding interfaces such as antennae that are able to send and/or receive these signals.

Figure 7:
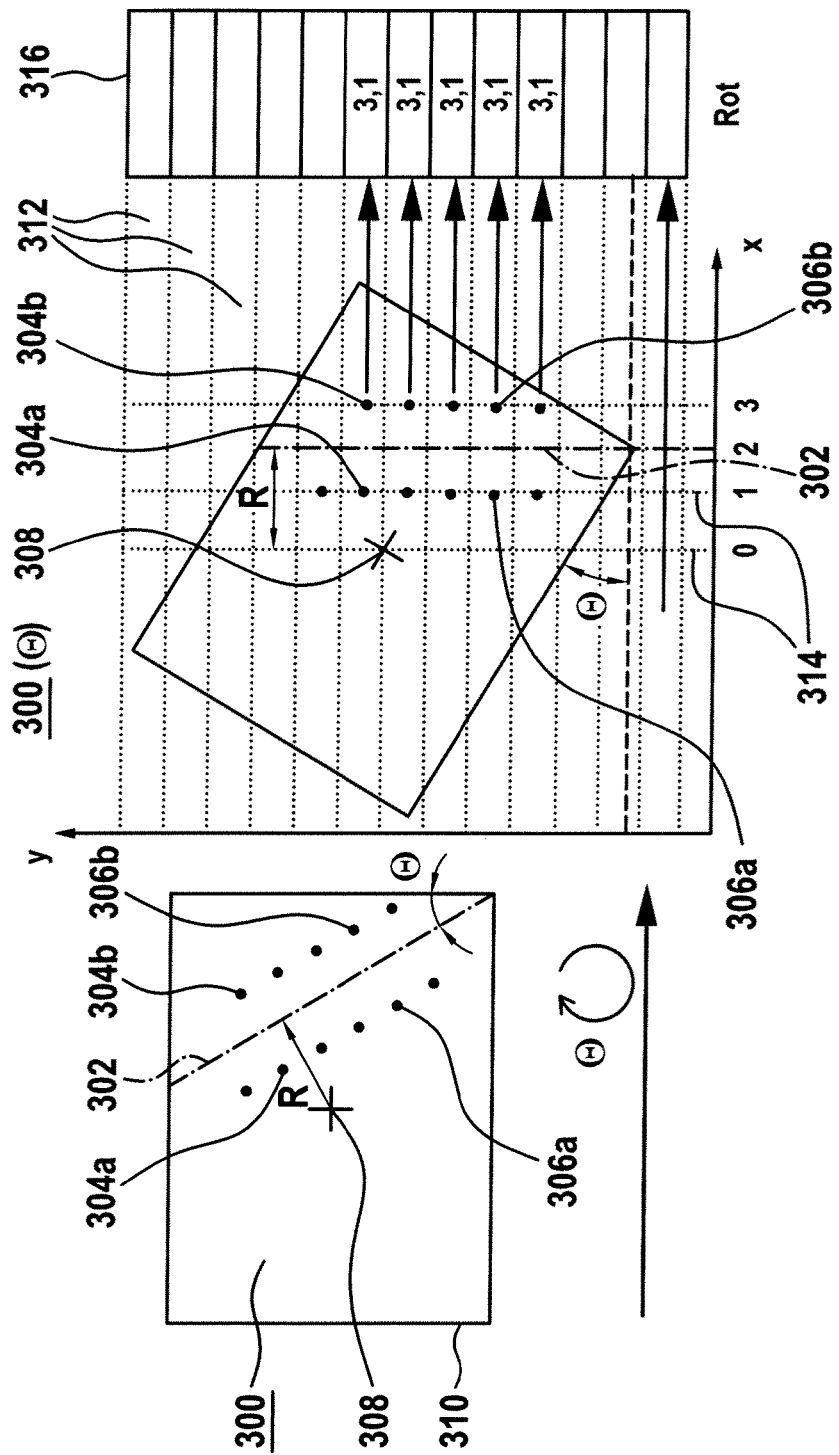
FIG. 7 shows a basic principle for detecting symmetry lines in an edge image.

FIG. 7 shows a possible basic principle for detecting symmetry lines in an edge image 300, which can, for example, be the edge images 1b and 40b of FIGS. 2 and 4; the depiction in FIG. 7 can be traced back to the publication mentioned at the beginning by Li, Zhang, and Kleeman, "Real Time Detection and Segmentation of Reflectionally Symmetric Objects in Digital Images," Proceedings of the 2006 IEEE/RSJ, International Conference on Intelligent Robots and Systems, Oct. 9-15, 2006, Beijing, China.

In the depiction in FIG. 7, it is assumed that there is the edge image 300 to be searched for symmetry lines. A possible symmetry line 302 is determined by means of pairs of edge picture elements 304a, 304b and 306a, 306b that lie symmetrical to this line. For the sake of simplicity here, only two examples for edge picture element pairs are provided with reference numerals; edge picture elements of a pair are characterized by the same reference numerals, with the points of a pair being distinguished by means of the additional lower case letters assigned to them.

The symmetry line 302 sketched in as an example in the edge image 300 can be described by its distance from the image center point 308 and by an angle $\Theta$ that can be defined relative to a definite reference line such as the vertical image edge 310.

A basic principle of detecting symmetry lines is constituted by rotating the edge image 300 through an angular range from 0 to 180° (0 to $\pi$) in fixed angular steps, for example of 1° each and then searching in the rotated edge image for vertically extending symmetry lines possibly contained in the edge image. The current rotation angle $\Theta$ of the edge image 300 corresponds to the angle of a symmetry line detected in the respective step.

In order to find the symmetry line 302, for example as shown on the right side in FIG. 7, the edge image 300 is analyzed from left to right for each possible vertical position 314, by searching line 312 by line 312—with the assumption that a symmetry line is situated at a position 314—for the edge picture element pairs (302a, 302b), (304a, 304b) that match a symmetry line in the respective column position 314. The edge picture element pairs determined in this way are assembled into a matrix Rot 316 for each column position. If all of the lines 312 for a particular column position 314 have been completed, then the number of all of the edge picture element pairs that have matched a possible symmetry line at the associated column position 314 can be taken as a result value for the assumption that a symmetry line is present at this location. In FIG. 7, the columns point in the x direction starting from the image center point (x). In the fields of the matrix Rot 316, the x coordinates of the edge picture element pairs that match the symmetry axis 302 are noted for each line 312; these are correspondingly the x values 3 and 1. For each rotation angle $\Theta$, after one full pass through all of the column positions 314, there is a result value for each column position, i.e. for each x value. The symmetry lines that are possibly present in the edge image 300 are detected based on this frequency distribution across the column positions x.

The preceding paragraph is a simplified depiction of the procedure. For more details, reference is made to the above-mentioned publication, whose content—as already stated previously—is incorporated herein by reference.

The proposed improvement aspects for avoiding the detection of pseudo-symmetry lines will be explained below based on FIGS. 8 and 9.

As has been demonstrated with FIGS. 1 through 4 based on real X-ray images, edges of individual items contained in the X-ray image are detected and a corresponding edge image 1a, 40a is produced (FIGS. 2 and 4).

Figure 8:
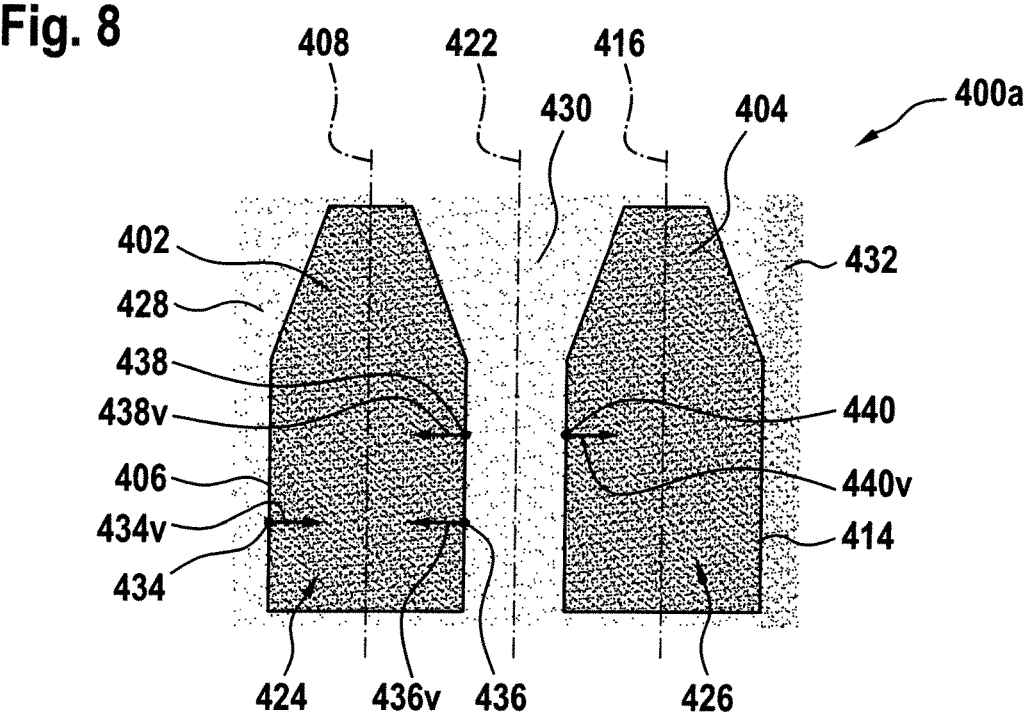
FIGS. 8 and 9 use a simplified X-ray image and the associated edge image to illustrate improvement aspects for avoiding the detection of pseudo-symmetry lines.

FIG. 8 shows a simplified depiction of an X-ray image 400a.

Then, as schematically explained with reference to FIG. 7, possible symmetry lines are determined for the items with symmetry properties that are contained in the X-ray image. This takes place, as shown in FIG. 7, based on pairs of edge picture elements (304a, 304b), (306a, 306b) of the edge image 300 that are positioned symmetrically to each other with reference to the respective symmetry line.

Figure 9:
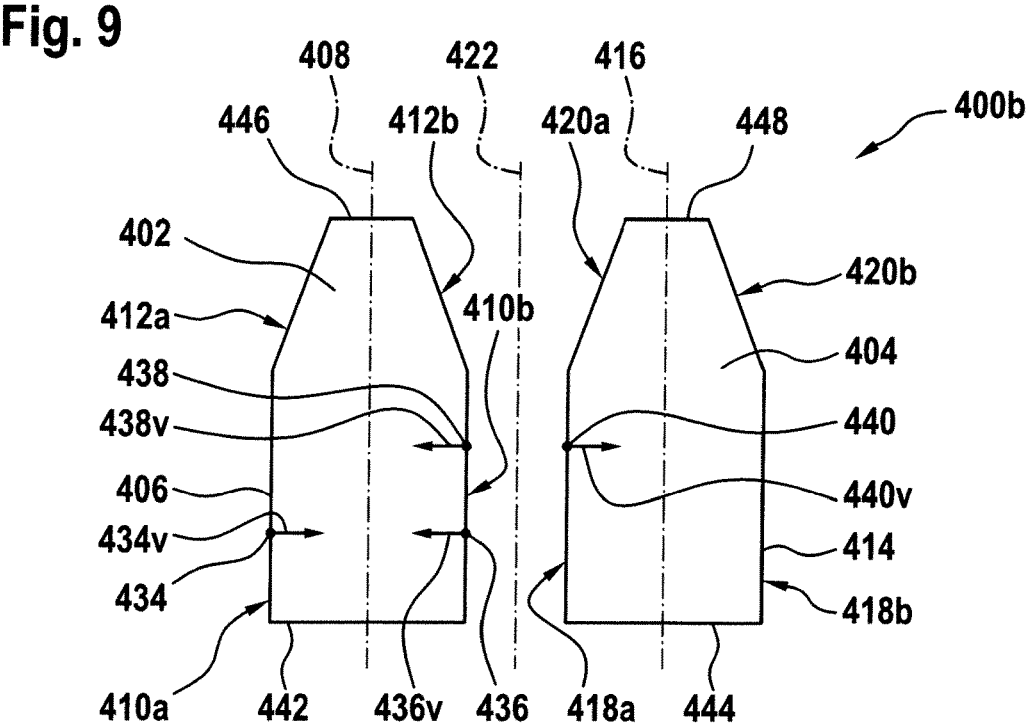

FIG. 9 shows an edge image 400b that belongs to the X-ray image 400a in FIG. 8 produced by means of edge filter preprocessing. The detail contains only a first item 402 and a second item 404 with symmetry properties.

The first item has a first outline 406 and symmetrical to a first symmetry line 408. In addition, left outer edge sections 410a and 412a of the first item 402 are symmetrical to right outer edge sections 410b and 412b. The second item 404 has a second outline 414 and symmetrical to a second symmetry line 416. In addition, left outer edge sections 418a and 420a of the second item 404 are symmetrical to right outer edge sections 418b and 420b.

Because of how the algorithm for detecting symmetry lines explained above with reference to FIG. 7 works, it will also detect a third symmetry line 422. The X-ray image 400 does not contain any real item that relates to the third symmetry line 422. Consequently, the symmetry line 422 is a pseudo-symmetry line. Pseudo-symmetry lines of this kind can result in the fact that incorrect regions in an X-ray image are identified and marked as an item. This may be avoided.

As explained above, it is possible in the X-ray image 400a to recognize which side of the outer edges 410a, 410b, 412a, 412b and 418a, 418b, 420a, 420b is the one in which image regions of the X-ray image 400a belong to one of the items 402 and 404. Since the X-ray image 400a is produced as a transmission image based on absorption of X-rays by materials positioned in the beam path, image regions 424 and 426 that can be associated with one of the items 402 and 404 in the X-ray image 400a are darker than image regions 428, 430, and 432 that belong to the surroundings of the items 402 and 404. For each edge or each edge picture element 434, 436, 438, 440, it is thus basically possible to determine which side of the respective edge of an item is the one on which the item lies. In other words, it is possible to determine the direction in which, starting from the respective edge, the image region lies within the associated item. In other words, the individual edges in the X-ray image can each be associated with a direction.

This is taken into account when detecting the symmetry line 408, 416 in order to avoid detecting the pseudo-symmetry line 422. To that end, in the search for symmetry lines in the edge image 400b that is explained based on FIG. 7, for an initially assumed symmetry line edge, picture elements for those edges for which the assumed symmetry line would lie outside of the item to which the edge belongs are not taken into account. Consequently, the search region for symmetry lines is effectively limited to image regions that lie inside an item.

The "correct" side of an edge is identified as belonging to an item contained in the X-ray image by comparing the X-radiation intensities measured in the X-ray image for picture elements on both sides of the edge under consideration. In principle, the image regions 424 and 426 for which predominantly lower intensity values exist—i.e. that are darker in the X-ray image 400a—are associated with the interior of an item 402 or 404.

To facilitate handling, for each edge picture element 434, 436, 438, 440, a vector 434v, 436v, 438v, 440v is stored in memory, which is defined so that starting from the associated edge 410a, 410b or 418a, it points or is oriented into the item 402 or 404 that belongs to the respective edge. Consequently the coordinates of an edge picture element, together with the vector, constitute a feature vector.

In the X-ray image 400a in FIG. 8 and in the edge image 400b in FIG. 9, this is respectively shown for two pairs (434, 436) and (438, 440) of edge picture elements. The edge picture elements 434 and 436 are symmetrical to the symmetry line 408. In accordance with the direction vectors 434v, 436v associated with these edge picture elements 434, 436, the symmetry line 408 lies in an image region 424 that can be associated with the item 402 in the X-ray image 400a. Consequently, the two edge picture elements 434, 436 are taken into account in the determination of the symmetry line 408. In other words, the two edge picture elements 434, 436 "vote" for the symmetry line 408. If, however, the direction vectors 438v, 440v associated with the edge picture elements 438, 440 are taken into account, then it is clear that the pseudo-symmetry line 422 lies in an image region 430 that cannot be associated with any of the items 402, 404 in the X-ray image 400a. To be specific, the direction vectors 438v, 440v point away from the pseudo-symmetry line 422. Consequently, the two edge picture elements 438, 440 are not taken into account in the symmetry line 422. In other words, the two edge picture elements 438, 440 do not "vote" for the symmetry line 422. By means of this improvement, pseudo-symmetry lines are given a lower result value in the approach depicted in FIG. 7 and are not identified as symmetry lines.

The improvement explained above can be taken into account with particular ease in the algorithm for detecting symmetry lines in that the direction vector associated with a picture element is only checked for whether it points toward or away from the symmetry line under consideration. In other words, for a possible symmetry line, the only edge picture elements that are used are those whose direction vector points toward a symmetry line under consideration.

The direction vector explained here does not absolutely have to be stored in memory for every individual edge picture element, but can instead also be determined and stored in memory for individual edge sections. For the individual edge picture element, the respective direction vector is then produced by means of the association with an edge.

By means of the direction vectors 434v, 436v, 438v, 440v the algorithm for detecting symmetry lines is made more robust. As a result, result the detection of pseudo-symmetry lines is cut in half.

Another improvement of the algorithm for detecting symmetry lines with regard to pseudo-symmetry lines and computation effort is achieved by the following measure, which can be used in addition or alternatively to the above-described improvements. In the method explained in conjunction with FIG. 7, the edge image 300 is incrementally rotated over a predetermined angular range and possible vertical symmetry lines 302 in the rotated edge image 300(Θ) are determined for each rotation angle Θ. To that end—as explained above—basically for each possible vertical symmetry line, it is determined which pairs of edge picture elements of the rotated edge image 300(Θ) can be associated with a particular symmetry line.

In FIG. 9, the edge image also contains horizontally extending edges 442, 444, 446, 448 that are likewise symmetrical relative to the respective symmetry lines 408, 416. Consequently, at first, it appears to be correct for the pairs of edge picture elements relative to the respective symmetry line 408, 416 that are identifiable on the edges 442, 444, 446, 448 to be taken into account for the determination of the respective symmetry line.

It has been determined, however, that in most cases, horizontally extending edges in the rotated edge image 300(Θ) do not belong to an item for which there is a vertical symmetry line in the rotated edge image 300(Θ). In other words, horizontal edges predominantly result in the detection of pseudo-symmetry lines in the rotated edge image 300(Θ).

Consequently the modification of the algorithm for avoiding the detection of pseudo-symmetry lines includes the provision that in the method shown in FIG. 7, for each rotation angle Θ, respective edge picture elements, which belong to the edge extending orthogonal to a symmetry line in the rotated edge image 300(Θ), for example the edges 442, 444, 446, 448 in FIG. 9, are not taken into account. This prevents such edge picture elements from being incorporated into the matrix Rot 316 in FIG. 7 and increasing a result value for a column, i.e. "voting" for a symmetry line that does not actually exist. This reduces the number of detected pseudo-symmetry lines. This also reduces the computation effort for the algorithm.

Particularly bottles as the items to be detected very often have—from almost every viewing direction—an outline that is largely composed of straight lines, i.e. of rectilinear edge regions. From a practical standpoint, this can be implemented while implementing the algorithm for detecting a symmetry line in that for each approximately rectilinear edge in the edge image, an edge direction vector is determined and stored in memory, e.g. for associated edge picture elements of the edge.

For example, in the edge image 400b in FIG. 9, the only edge picture elements of edge pairs that are taken into account in the determination of the symmetry line 408 are those that extend symmetrically to each other relative to the symmetry line 408. Since, for example, the edge direction vectors for the edges 410a and 410b can be derived from the direction vectors 434v and 436v of the two edge picture elements 434 and 436, it is possible for a plausibility test to be carried out for the edge picture elements 434 and 436 that are symmetrical to a symmetry line 408. In this connection, it is not even absolutely necessary to determine an edge direction vector. Instead, it is sufficient to check whether the respective direction vectors of the edge picture elements under consideration are complementary to each other, i.e. the two angles have to complement each other to 180° or 360°. If the check reveals that the edge direction vectors 434v and 436v under consideration extend symmetrically to each other in relation to the symmetry line 408, then the edge picture elements 434 and 436 are taken into account in the determination of the symmetry line 408; otherwise, they are not taken into account, i.e. do not flow into the matrix Rot 316 in the method shown in FIG. 7, i.e. they are not permitted to "vote" for the symmetry line 408.

The aim of the method is to segment, for example, the items 402 and 404 (FIG. 8) with symmetry properties in the edge image 400b (FIG. 9) based on the respectively associated symmetry line 408 or 416. To that end, the respective outline 406 or 414 (FIGS. 8 and 9) is determined for the items 402 and 404 (FIG. 8). The outlines 406, 414 are contour lines that are symmetrical to the respective symmetry line 408 or 416.

In X-ray images of pieces of luggage, as shown in den FIGS. 1 and 3, many items are contained in a jumble. As a result, individual items overlap one another in the X-ray image so that edges of the items in the X-ray image are hidden and are not clearly identifiable.

Figure 10:
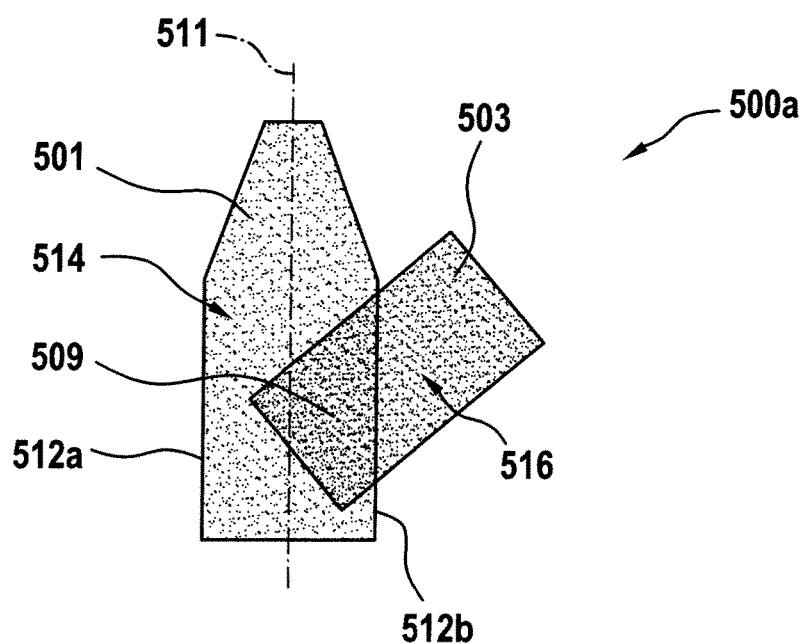
FIGS. 10 and 11 use a simplified X-ray image and the associated edge image to illustrate an improvement in the segmentation of items in the edge image when items are overlapping in the X-ray image.
Figure 11:
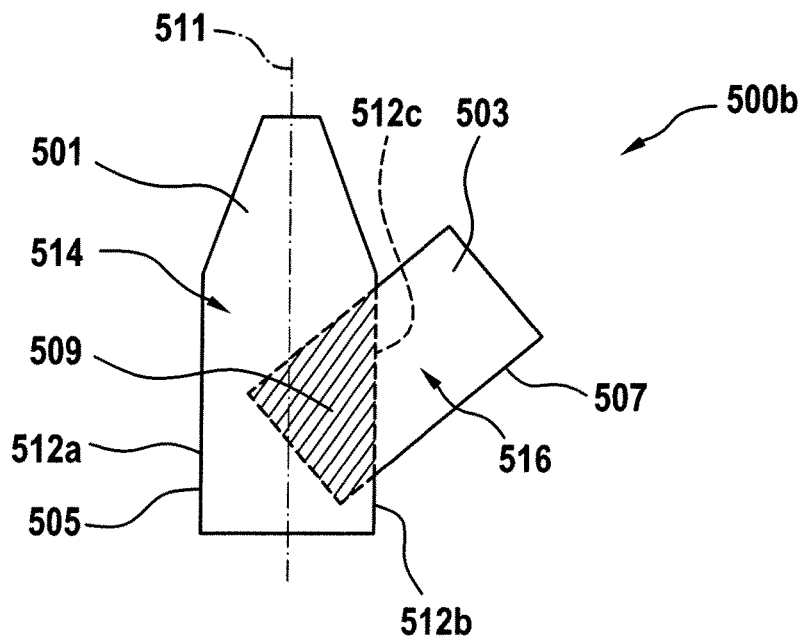

FIG. 10 shows a simplified X-ray image 500a and FIG. 11 shows the associated edge image 500b. In the X-ray image 500a, there are two items 501 and 503 that partially overlap each other. The two items 501 and 503 are shown with their respective outlines 505 and 507 in FIG. 11, with an overlap region 509 of the two items 501 and 503 being depicted with hatching. For the item 501, the symmetry line 511, which is shown in both FIG. 10 and FIG. 11, has been determined.

According to a modification of the method proposed here, two edges 512a and 512b, which have been determined to be symmetrical to the symmetry line 511 and in which there are missing edge picture elements in the edge 512b, are filled in mirror-symmetrically relative to the symmetry line 511 based on the edge 512a. The edge piece in the edge 512b that has been filled in is identified with the reference numeral 512c. The gap in the edge 512b of the outline 505 that is caused by the overlapping 509 is thus closed.

The overlap region 509, in which the item 501 and the edge 512b of the item 501 are partially overlapped by the other item 503, is determined based on X-ray intensities measured for picture elements associated with the overlap region 509. In the overlap region 509 in the X-ray image 500a, lower intensity values for X-rays were measured than in the image regions 514, 516 of the individual items 501, 503 without overlapping. The overlap region 509 is therefore darker in the X-ray image 500a than the non-overlapped image regions 514, 516.

This measure makes it possible to achieve a better segmentation of a partially hidden item 501 with a symmetry property.

Figure 12:
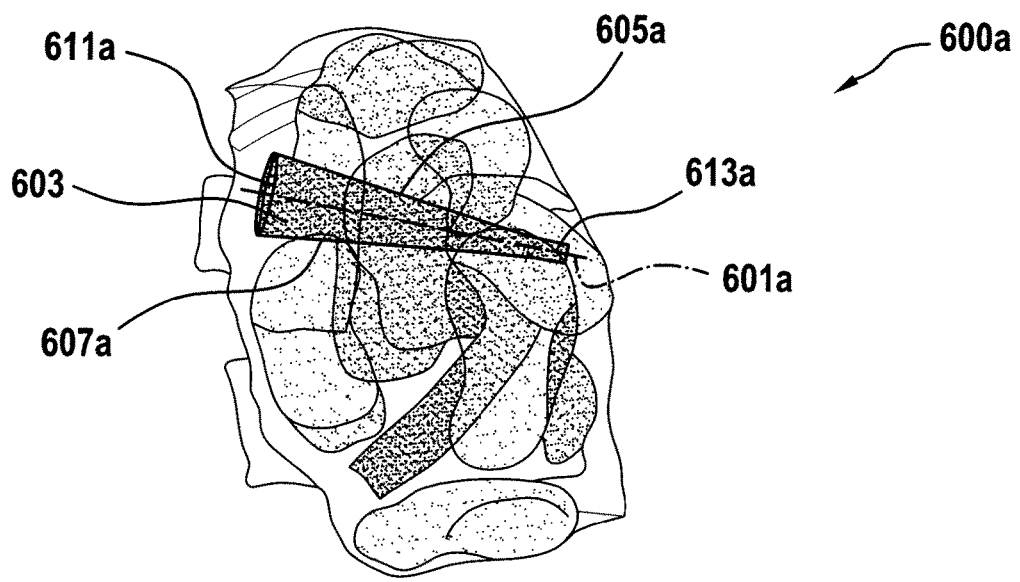
FIGS. 12 through 14 each show an X-ray image of the first piece of luggage in FIG. 1 from different viewing directions; edges that have been detected as belonging to a bottle and the detected symmetry line are shown in each of the X-ray images.
Figure 13:
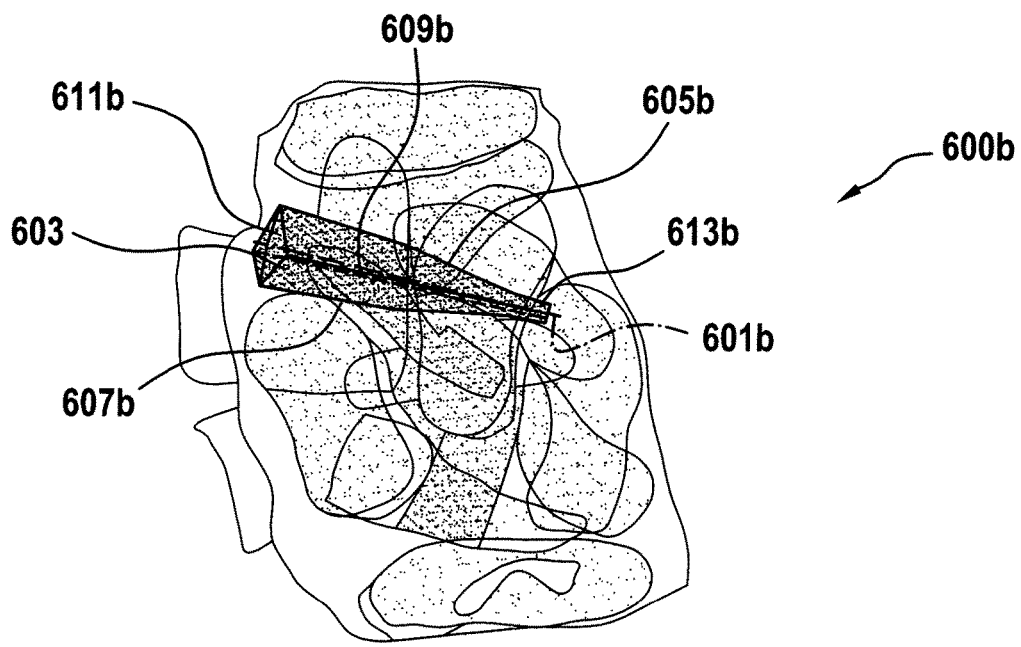
Figure 14:
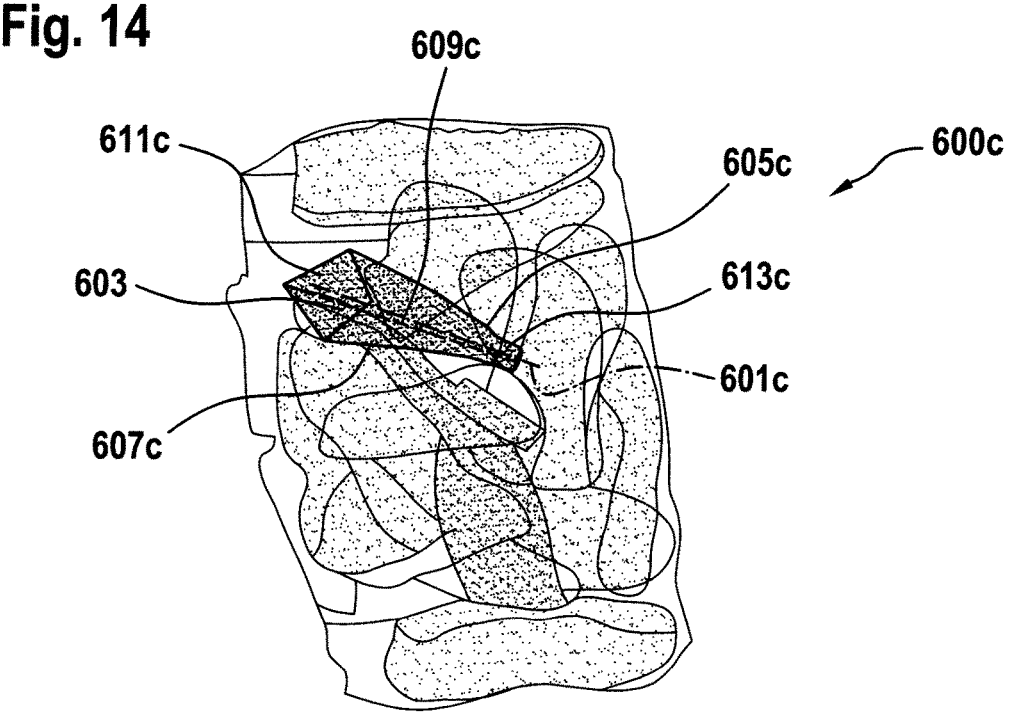

FIGS. 12 through 14 show another modification of the method. In this case, a respective symmetry line 601a, 601b, 601c has been determined for the same item with symmetry properties, namely a bottle 603, in at least three X-ray images 600a, 600b, 600c of the same inspection object from different respective irradiation directions. To produce X-ray images 600a, 600b, 600c, it is possible, for example, to use an X-ray inspection system of the kind that is known from DE 101 49 254 A1.

In the respective X-ray images 600a, 600b, 600c, it is also possible to respectively determine the bottom 611a, 611b, and 611c, respectively, of the bottle 603 and the neck 613a, 613b, and 613c, respectively, of the bottle 603, so as to be able to associate a direction with the respective symmetry lines 601a, 601b, 601c. These measures make the subsequent projections more stable.

The bottle 603 identified in the X-ray images 600a, 600b, 600c cannot be validated based on its identified outer edges, since the image regions in the X-ray images 600a, 600b, 600c are not equivalent. The bottle 603 can, however, be validated in the 3D space by means of the identified symmetry lines 601a, 601b, 601c in the individual X-ray images 600a, 600b, 600c. The individual symmetry line 601a, 601b, 601c of the X-ray images 600a, 600b, 600c, taken in and of themselves, are not clearly determined in the 3D space. Each symmetry line 601a, 601b, 601c corresponds to a corresponding symmetry plane in the 3D space. Whether the symmetry lines 601a, 601b, 601c determined in the three different X-ray images 600a, 600b, 600c belong to the same bottle 603 can be checked by means of a projection of the symmetry lines 601a, 601b, 601c into the three-dimensional (3D) space. If the same bottle 603 has actually been detected in all of the X-ray images 600a, 600b, 600c, then theoretically, the three intersecting lines of two respective symmetry planes in the 3D space coincide. In practice, these intersecting lines are adjacent to one another at least within a particular tolerance range and at least have the same direction. If this condition is fulfilled, then the bottle 603 and the symmetry line 601a, 601b, 601c determined in the X-ray images 600a, 600b, 600c count as validated.

Based on the respectively segmented image regions in the three X-ray images 600a, 600b, 600c associated with the bottle 603, a three-dimensional model of the bottle 603 has been determined. Since for the individual X-ray image 600a, 600b, or 600c, the respective direction from which the inspection object has been irradiated is known, based on the 3D model, the outer edges 605a, 607a; 605b, 607b; and 605c, 607c and the respective symmetry line 601a, 601b, or 601c of the bottle 603 are projected into the respective X-ray image 600a, 600b, or 600c. The bottle 603 is thus easier to recognize for an operator of the X-ray inspection system.

In some embodiments, initially invisible edges 609a, 609b, and 609c, respectively, are projected into the respective X-ray image 600a, 600b, and 600c, respectively. The bottle 603 is then even easier to recognize for an operator of the X-ray inspection system.

By the projection of edges in the respective X-ray image 600a, 600b, or 600c of the detected bottle 603 and of the detected symmetry line 601a, 601b, or 601c into the three-dimensional (3D) space, it is possible to validate the bottle 603 and the detected symmetry lines 601a, 601b, and 601c, respectively.

The invention claimed is:

1. A method for detecting a three-dimensional item inside an inspection object, the method comprising:
   detecting edges of a plurality of items contained in a transmission image of an inspection object in order to produce an edge image, at least some of the items being three-dimensional; and
   detecting within the plurality of items a three-dimensional item having at least one symmetry property by determining a symmetry line of the items contained in the transmission image, the three-dimensional item having at least one symmetry property comprising a bottle, the symmetry line determined by detecting pairs of edge picture elements of the edge image that are positioned symmetrically to each other relative to the symmetry line that is to be determined, wherein, in the determining a symmetry line in the edge image, the only edge picture elements that are taken into account are those for which the symmetry line in the transmission image lies in the image region of the three-dimensional item to which the edge picture elements belong, determining, in the respective transmission images, a direction for the respective symmetry line by determining a bottom of the bottle and a neck of the bottle in the respective transmission images based on a difference in thickness between the bottom of the bottle and the neck of the bottle; and
   producing an output classification associated with the item detected.

2. The method according to claim 1, further comprising:
   determining at least one feature descriptor for at least one image region in the vicinity of a selected edge picture element in the transmission image; and
   comparing the at least one feature descriptor to reference values in order to validate the selected edge picture element as an outer edge of a container.

3. The method according to claim 1, wherein detecting the three-dimensional item having at least one symmetry property includes making a determination, based on intensity values of individual picture elements in the transmission image, as to which side of an edge under consideration is the one in which an image region of the transmission image can be associated with the item belonging to the edge.

4. The method according to claim 1, wherein the edge image is produced based on material information associated with individual picture elements of the transmission image.

5. The method according to claim 1, wherein respective edge picture elements of edges extending orthogonal to a symmetry line are not taken into account in the determining of a symmetry line.

6. The method according to claim 1, wherein the edge picture elements are only taken into account in the determining of a symmetry line if the respective edge picture elements have edge angles relative to the symmetry line that complement one another to 180° or 360°.

7. The method according to claim 1, further comprising: segmenting of a three-dimensional item with symmetry properties in the edge image by determining an outline of the item; wherein when there are two determined edges that are determined to be symmetrical to a symmetry line, missing parts of the edges are filled in mirror-symmetrically to the symmetry line if the missing parts lie in an overlap region in which the item and the edge of the item are partially overlapped by another item; and wherein the overlap region is determined based on intensity values in the transmission image.

8. The method according to claim 1, wherein detecting a three-dimensional item with at least one symmetry property further comprises detecting the three-dimensional item with at least one symmetry property in at least three transmission images of the same inspection object from different irradiation directions.

9. The method according to claim 1, wherein producing an output classification associated with the item detected comprises inferring a content of the item detected based on at least one of the transmission image or the edge image and an outer material of the item detected.

10. The method according to claim 1, wherein producing an output classification associated with the item detected comprises determining whether the item poses a security risk.

11. The method according to claim 1, wherein the inspection object comprises a piece of luggage.

12. The method according to claim 8, further comprising: validating of symmetry lines through projection in to a 3D space; and inspecting the position of intersecting lines of the symmetry planes in the 3D space relative to one another.

13. A system for detecting an item inside an inspection object, the system comprising:
an inspection device configured to obtain a transmission image of an inspection object;
at least one computing device in communication with the inspection device the at least one computing device including:
a memory configured to store code;
a processor coupled to the memory, the processor configured to execute the code to cause the processor to:
receive a transmission image from the inspection device;
detect edges of a plurality of items contained in a transmission image of an inspection object in order to produce an edge image, at least some of the items being three-dimensional; and
detect within the plurality of items a three-dimensional item having at least one symmetry property by determining a symmetry line of the items contained in the transmission image, the three-dimensional item having at least one symmetry property comprising a bottle, the symmetry line determined by detecting pairs of edge picture elements of the edge image that are positioned symmetrically to each other relative to the symmetry line that is to be determined, wherein, in the determining a symmetry line in the edge image, the only edge picture elements that are taken into account are those for which the symmetry line in the transmission image lies in the image region of the three-dimensional item to which the edge picture elements belong, determining, in the respective transmission images, a direction for the respective symmetry line by determining a bottom of the bottle and a neck of the bottle in the respective transmission images based on a difference in thickness between the bottom of the bottle and the neck of the bottle; and
produce an output classification associated with the item detected.

14. The system according to claim 13, wherein the inspection device comprises an X-ray inspection system configured for producing at least one X-ray image of the inspection object.

15. The system according to claim 14, wherein the X-ray inspection system includes:
a transport apparatus leading through an irradiation tunnel, the transport apparatus configured to receive the inspection object;
at least one X-ray source arrayed around the transport apparatus, the X-ray source configured to emit X-rays in at least two different irradiation planes to irradiate the inspection object; and
at least one detector array oriented in each of the at least two different irradiation planes; the at least one detector array configured to measure at least one intensity associated with the X-rays.

16. The method according to claim 13, wherein the inspection object comprises a piece of luggage.

17. A method for detecting a three-dimensional item inside an inspection object, the method comprising:
detecting edges of a plurality of items contained in a transmission image of an inspection object in order to produce an edge image, at least some of the items being three-dimensional; and
detecting within the plurality of items a three-dimensional item having at least one symmetry property by determining a symmetry line of the items contained in the transmission image, the three-dimensional item having at least one symmetry property comprising a bottle, the symmetry line determined by detecting pairs of edge picture elements of the edge image that are positioned symmetrically to each other relative to the symmetry line that is to be determined, wherein, in the determining a symmetry line in the edge image, the only edge picture elements that are taken into account are those for which the symmetry line in the transmission image lies in the image region of the three-dimensional item to which the edge picture elements belong;
segmenting of a three-dimensional item with symmetry properties in the edge image by determining an outline of the item, wherein when there are two determined edges that are determined to be symmetrical to a symmetry line, missing parts of the edges are filled in mirror-symmetrically to the symmetry line if the missing parts lie in an overlap region in which the item and the edge of the item are partially overlapped by another item, and wherein the overlap region is determined based on intensity values in the transmission image; and producing an output classification associated with the item detected.

* * * * *